United States Patent
Xu et al.

(10) Patent No.: US 10,710,945 B2
(45) Date of Patent: Jul. 14, 2020

(54) AROMATIC COMPOSITIONS AND METHODS FOR OBTAINING THEM

(71) Applicant: ExxonMobil Chemical Patents Inc., Baytown, TX (US)

(72) Inventors: Teng Xu, Houston, TX (US); Stephen M. Davis, Dawsonville, GA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 190 days.

(21) Appl. No.: 15/753,023

(22) PCT Filed: Aug. 3, 2016

(86) PCT No.: PCT/US2016/045226
§ 371 (c)(1),
(2) Date: Feb. 15, 2018

(87) PCT Pub. No.: WO2017/052790
PCT Pub. Date: Mar. 30, 2017

(65) Prior Publication Data
US 2018/0237361 A1 Aug. 23, 2018

Related U.S. Application Data

(60) Provisional application No. 62/232,715, filed on Sep. 25, 2015.

(51) Int. Cl.
| | |
|---|---|
| C07C 2/74 | (2006.01) |
| C07C 5/367 | (2006.01) |
| C07C 41/09 | (2006.01) |
| C09K 5/10 | (2006.01) |
| C07C 45/53 | (2006.01) |
| C07C 407/00 | (2006.01) |
| C07C 37/08 | (2006.01) |
| C07C 6/12 | (2006.01) |
| C07C 13/18 | (2006.01) |
| C07C 409/14 | (2006.01) |

(52) U.S. Cl.
CPC .............. *C07C 5/367* (2013.01); *C07C 2/74* (2013.01); *C07C 6/126* (2013.01); *C07C 13/18* (2013.01); *C07C 37/08* (2013.01); *C07C 41/09* (2013.01); *C07C 45/53* (2013.01); *C07C 407/00* (2013.01); *C09K 5/10* (2013.01); *C07C 409/14* (2013.01); *C07C 2601/14* (2017.05); *C07C 2601/16* (2017.05)

(58) Field of Classification Search
None
See application file for complete search history.

(56) References Cited

U.S. PATENT DOCUMENTS

| | | | |
|---|---|---|---|
| 3,356,456 A | 12/1967 | Wilson | |
| 3,962,362 A * | 6/1976 | Suggitt | ............ C07C 2/74 585/252 |
| 4,810,279 A | 3/1989 | Martin | |
| 5,075,022 A | 12/1991 | Gambell et al. | |
| 5,459,122 A | 10/1995 | Ford et al. | |
| 5,972,971 A | 10/1999 | Heuer et al. | |
| 6,797,193 B2 | 9/2004 | Brown et al. | |
| 8,247,627 B2 | 8/2012 | Dakka et al. | |
| 2005/0215433 A1 | 9/2005 | Benitez et al. | |
| 2011/0146959 A1 * | 6/2011 | Root | ............ C09K 5/10 165/108 |
| 2013/0172514 A1 * | 7/2013 | Xu | ............ C07C 2/74 528/212 |
| 2013/0296614 A1 * | 11/2013 | Kuechler | ............ B01J 21/00 568/798 |
| 2014/0275606 A1 | 9/2014 | Bai et al. | |

FOREIGN PATENT DOCUMENTS

| | | |
|---|---|---|
| JP | 52-038005 A | 3/1977 |
| JP | 05-212705 B | 6/2013 |
| WO | 2015/094530 A | 6/2015 |

OTHER PUBLICATIONS

Moens, L., et al., "Mechanism of Hydrogen Formation in Solar Parabolic Trough Receivers", Technical Report NREL/TP-510-42468, Feb. 2008.

* cited by examiner

*Primary Examiner* — Philip Y Louie
(74) *Attorney, Agent, or Firm* — Kevin M. Faulkner

(57) ABSTRACT

Aromatic compositions useful in various applications, such as aromatic fluid solvents and high temperature heat transfer fluids, are provided herein. Also provided are advantageous methods for obtaining the aromatic compositions, utilizing hydroalkylation of precursor aromatic hydrocarbons such as benzene, toluene, xylene, and the like. Particularly preferred aromatic compositions include one or more of cycloalkylaromatic, dicycloalkylaromatic, biphenyl, terphenyl, and diphenyl oxide compounds. The aromatic compositions may be blended with an aromatic solvent or other aromatic fluid comprising one or more of alkylnaphthalenes, alkylbenzenes, and naphthalene, e.g., to form a useful aromatic fluid solvent, or the aromatic compositions may be utilized as high temperature heat transfer fluids (with or without additional blend components).

13 Claims, No Drawings

AROMATIC COMPOSITIONS AND METHODS FOR OBTAINING THEM

CROSS-REFERENCE TO RELATED APPLICATIONS

This application is a National Phase Application claiming priority to PCT Application Serial No. PCT/US2016/045226 filed Aug. 3, 2016, and also claims priority to U.S. Provisional Application U.S. Ser. No. 62/232,715, filed Sep. 25, 2015, both of which are hereby incorporated by reference in their entirety.

FIELD

This disclosure relates to multi-ring aromatic compounds (e.g., cycloalkyl-aromatic compounds and/or biphenyl compounds), their production, and uses thereof. In particular, the disclosure relates to multi-ring aromatic fluids that may be formed from processes including the hydroalkylation of benzene and/or alkyl-substituted benzenes, or the related alkylation of benzene and/or alkyl-substituted benzenes with cyclic olefins. Exemplary uses of such multi-ring aromatic compositions include agricultural solvents and high-temperature heat transfer fluids, such as those used in the refining and chemical industries and the harvesting of solar energy.

BACKGROUND

The production of cycloalkyl-aromatic compounds via hydroalkylation of benzenes and/or alkylbenzenes, and/or via alkylation of benzenes and alkylbenzenes with cyclic olefins, is an emerging technology. For instance, the hydroalkylation of benzene forms a composition comprising the cycloalkyl-aromatic compound cyclohexylbenzene, as well as other cycloalkyl-aromatic compounds such as methylcyclopentylbenzene and di-cyclohexylbenzene as byproducts. Such a hydroalkylation is described in numerous references, for instance as part of an integrated process for the production of cyclohexanone and/or phenol. See, for example, U.S. Pat. No. 8,247,627 and WIPO Patent Publication No. WO 2015/094530.

Other exemplary processes include hydroalkylation of alkylbenzenes such as toluene and/or xylene to form multi-ring aromatic compounds such as (methylcyclohexyl)toluene and/or (dimethylcyclohexyl)xylene, as described, e.g., in U.S. Patent Publication No. 2014/0275606. Such compounds, it is disclosed, are capable of being further processed to form additional multi-ring aromatic compounds such as methyl-substituted biphenyl compounds (including by dehydrogenation).

The present inventors have recognized that many of the aromatic compounds, and particularly multi-ring aromatic compounds such as those produced in the exemplary processes noted above, may be recovered and used in other applications suitable for aromatics fluids, such as agricultural solvents and high-temperature heat transfer fluids in solar energy applications. Such aromatics fluids are typically sourced from reformate fractions produced during the refining of crude oil and gas hydrocarbons. Such aromatics fractions may be characterized as set forth, e.g., in U.S. Pat. No. 5,459,122, as having a naphthenebenzenes and dinaphthenebenzenes content of at least 50 wt % based on the aromatics fraction. Examples of aromatics fluids currently used in industry include agricultural solvents such as Aromatic 100, Aromatic 150, and Aromatic 200 fluid products, available from ExxonMobil Chemical Company. For instance, the Aromatic 200 fluid products typically may comprise approximately 25 to 30 components, with some of the principle components comprising fused-ring aromatics such as various alkyklnaphthalenes (e.g., 2-methylnaphthalene, 1-methylnaphthalene, 2-ethyl-naphthalene, dimethyl naphthalenes, and trimethyl naphthalenes); as well as alkylbenzenes.

Unconventional sources for blend components and/or substitutes of such aromatics fluids, such as cycloalkylaromatics formed in the aforementioned hydroalkylation processes, may provide attractive alternatives for aromatics fluids, and/or for blending components for use in aromatics fluids, in addition to (or instead of) the traditional reformate fractions.

Similarly, such processes may provide attractive alternatives for high-temperature heat transfer fluid (HTHTF) components, such as biphenyl, terphenyl, and other substituted or unsubstituted multi-aryl compounds useful in, e.g., solar energy harvesting applications.

Several commercially available heat transfer fluids are known to contain biphenyls, terphenyls, and related compounds. For example, Dowtherm™ systems marketed by Dow Chemical Company reportedly contain biphenyls in combination with diphenyl ether. As another example, U.S. Pat. No. 5,075,022 discloses systems containing terphenyls. One drawback for systems containing no-substituted biphenyl is gradual decomposition to (environmentally unfriendly) benzene with long term aging and use.

Some additional references of interest in this regard include: U.S. Pat. Nos. 3,356,486; 4,810,279; 5,459,122; 5,972,971; and 6,797,193; as well as U.S. Patent Publication No. 2005/0215433, Japanese Patent Nos. 05-212705 and 52-038005; and L. Moens and D. Blake, *Mechanism of Hydrogen Formation in Solar Parabolic Trough Receivers*, NREL Technical Report NREL/TP-510-42468, February 2008.

SUMMARY

The present invention provides for aromatics fluids comprising multi-ring aromatic compounds such as cycloalkylaromatic compounds, dicycloalkylaromatic compounds, biphenyl compounds, terphenyl compounds, and/or diphenyl oxides formed via processes including hydroalkylation and/or transalkylation; and the processes for forming and formulating such aromatics fluids. Advantageously, such processes provide attractive alternatives to traditional sources for aromatics fluids such as aromatic solvents and HTHTFs.

Accordingly, the invention in some aspects includes obtaining a first aromatic composition from one or more precursor aromatic hydrocarbons. The first aromatic composition comprises one or more of various cycloalkylaromatic compounds, dicycloalkylaromatic compounds, biphenyl compounds, and/or terphenyl compounds (and/or substituted analogs). In some embodiments, the composition also or instead comprises one or more substituted or unsubstituted diphenyl oxides.

The invention in some embodiments further comprises blending the first aromatic composition with a second aromatic composition comprising one or more of naphthalene, alkylnaphthalenes, and alkylbenzenes (preferably comprising alkylnaphthalenes and alkylbenzenes), thereby forming a blended aromatic fluid composition.

In yet other embodiments, the first aromatic composition is formed into a high temperature heat transfer fluid. Forming the first aromatic composition into a high temperature heat transfer fluid may be as simple as blending the components of the first aromatic composition together to form the heat transfer fluid, or in some aspects, it may further include purifying the first aromatic composition, e.g., by separating one or more undesired components from the first aromatic composition.

Obtaining the first aromatic composition from the one or more precursor aromatic hydrocarbons according to some aspects includes a process comprising hydroalkylating the precursor aromatic hydrocarbon(s) so as to produce a hydroalkylation reaction effluent comprising (i) one or more cycloalkylaromatic compounds and (ii) one or more dicycloalkylaromatic compounds. According to other aspects, the process also or instead includes transalkylation (e.g., transalkylating the one or more precursor aromatic hydrocarbons with a precursor cycloalkylaromatic compound in the presence of a transalkylation catalyst so as to produce a transalkylation reaction effluent comprising the one or more cycloalkylaromatic compounds and the one or more dicycloalkylaromatic compounds).

In yet further aspects, the process of obtaining the first aromatic composition (whether including hydroalkylation, transalkylation, or both) further includes dehydrogenating at least a portion of the cycloalkylaromatic compounds and/or the dicycloalkylaromatic compounds, thereby obtaining the one or more biphenyl compounds and/or the one or more terphenyl compounds, such that the first aromatic composition comprises the one or more biphenyl compounds and/or the one or more terphenyl compounds.

In particular embodiments, obtaining the first aromatic composition comprises: (i) hydroalkylating one or more of cyclohexylbenzene, toluene, and one or more isomers of xylene, thereby obtaining a hydroalkylation effluent comprising substituted or unsubstituted cyclohexylbenzenes, substituted or unsubstituted dicyclohexylbenzenes, and, optionally, alkylcyclopentylbenzenes (such as methylcyclopentylbenzene and/or dimethylcyclopentylbenzene).

Processes according to some of these embodiments may further include: (ii) dehydrogenating a first portion of the hydroalkylation effluent or the transalkylation effluent so as to obtain a dehydrogenation effluent comprising one or more biphenyl compounds and/or one or more terphenyl compounds; and (iii) blending at least a portion of the dehydrogenation effluent with a second portion of the hydroalkylation effluent or the transalkylation effluent to form the first aromatic composition, such that the first aromatic composition comprises biphenyl compounds and/or terphenyl compounds in addition to the substituted or unsubstituted cyclohexylbenzenes, substituted or unsubstituted dicyclohexylbenzenes, and, optionally, alkylcyclopentylbenzenes.

Processes according to yet further embodiments further include: (iv) oxidizing a third portion of the hydroalkylation effluent or the transalkylation effluent so as to obtain an oxidation effluent comprising cyclohexylbenzene-hydroperoxide and/or alkyl-substituted cyclohexylbenzene hydroperoxides; (v) cleaving at least a portion of the oxidation effluent so as to obtain cyclohexanone (and/or alkyl-substituted cyclohexanones) and phenol (and/or alkyl-substituted phenols); (vi) dehydrating the phenol and/or alkyl-substituted phenols to obtain diphenyl oxides (and/or alkyl-substituted diphenyl oxides), and (vii) blending the diphenyl oxides and/or alkyl-substituted diphenyl oxides into the first aromatic composition. These diphenyl oxides may be particularly useful where the first aromatic composition is to be used as a HTHTF.

DETAILED DESCRIPTION OF THE EMBODIMENTS

The present invention provides for processes that provide advantageous alternative sources (and, in some cases, unconventional compounds) for use in aromatics fluids such as aromatic solvents and/or high temperature heat transfer fluid applications. Thus, the present invention in some embodiments also provides novel compositions of matter (useful as, e.g., aromatics solvents and/or HTHTFs).

The processes of various embodiments generally include obtaining a first aromatic composition from one or more precursor hydrocarbons. The first aromatic composition is then provided for its further use. For instance, in some embodiments, the first aromatic composition is blended with a second aromatic composition comprising one or more components of a typical aromatic solvent so as to form a blended aromatic fluid useful as an aromatic solvent. The blended aromatic fluid may have comparable properties to aromatic solvents, but provides an advantageous alternative source for certain key components of the solvents (e.g., cycloalkylaromatic, dicycloalkylaromatic, biphenyl, and/or terphenyl compounds). In some embodiments, the blended fluid includes components not conventionally used in such aromatic solvents. These unconventional components, in addition to being conveniently sourced, may provide advantageous properties to the aromatic solvents.

In other embodiments, the first aromatic composition is formed into a high temperature heat transfer fluid, either by blending the components of the first aromatic composition together, or by further purification of the first aromatic composition. The high temperature heat transfer fluid may similarly comprise unconventional compounds that provide advantageous properties to the heat transfer fluid. For instance, when substituted benzenes are used as a building block in accordance with some embodiments of the present invention, the problematic decomposition to benzene (seen in conventional HTHTFs) is advantageously avoided; instead, less deleterious products are formed from long-term decomposition. Moreover, product cold flow properties are improved when methyl-substituted benzene building blocks (such as toluene) are utilized.

Preferably, obtaining the first aromatic composition includes hydroalkylation and/or transalkylation processes, which have seen a great deal of recent development. These processes are capable of taking precursor aromatic hydrocarbons not normally useful in aromatic solvents and/or HTHTFs (e.g., benzene and alkyl-substituted benzenes such as toluenes, xylenes, ethylbenzenes, diethylbenzenes, and the like), and converting such precursor aromatic hydrocarbons to multi-ring structures such as cycloalkylaromatics and dicycloalkylaromatics that are useful in aromatic solvent and/or HTHTF applications. Further, dehydrogenation of at least a portion of the product effluents from hydroalkylation and/or transalkylation readily provide biphenyl and terphenyl compounds that are also useful in aromatic solvents, and which may be particularly useful in HTHTF applications.

The first aromatic composition of various embodiments, and the processes for obtaining such composition according to various embodiments herein, are each discussed in greater detail below.

Definitions

As used herein, the numbering scheme for the Periodic Table Groups is as disclosed in Chemical and Engineering News, 63(5), 27 (1985).

As used herein, a "$C_x$ hydrocarbon," where x is an integer, refers to a hydrocarbon compound having X carbon atoms. Thus, a $C_6$ hydrocarbon is a hydrocarbon having 6 carbon atoms. A "$C_x$-$C_y$ hydrocarbon" or a "$C_{x-y}$ hydrocarbon" is a hydrocarbon having from x to y carbon atoms, inclusive (e.g., a $C_6$-$C_{10}$ or $C_{6-10}$ hydrocarbon is a hydrocarbon having 6, 7, 8, 9, or 10 carbon atoms); a "$C_x$ or greater" hydrocarbon is a hydrocarbon having x or more carbon atoms; and a "greater than $C_x$ hydrocarbon" is a hydrocarbon having more than x carbon atoms. Similarly, a "$C_x$ or less" hydrocarbon is one having x or fewer carbon atoms, and "a less than $C_x$" hydrocarbon is one having fewer than x carbon atoms.

At certain points herein, reference is made to various "$C_n$" compounds. In such instances, unless otherwise indicated, n may be an integer ranging from 6 to 12, inclusive. Along these lines, a "$C_{2n}$" hydrocarbon is therefore a hydrocarbon having 2*n carbon atoms, with reference to a $C_n$ hydrocarbon, and a "$C_{3n}$" hydrocarbon is similarly a hydrocarbon having 3*n carbon atoms. For instance, where a $C_n$ hydrocarbon is given as a $C_7$ hydrocarbon (e.g., toluene), a $C_{2n}$ hydrocarbon would be a $C_{14}$ hydrocarbon. Where a mixture of multiple species of $C_6$-$C_{12}$ hydrocarbons is referred to, the $C_n$ hydrocarbon will be the smallest (least number of carbon atoms) among those $C_6$-$C_{12}$ hydrocarbons (thus, the mixture may be referred to as being of, e.g., $C_n$-$C_{12}$ hydrocarbons). Similarly, where a mixture of $C_{12}$-$C_{24}$ hydrocarbons is referred to, the $C_{2n}$ hydrocarbon will be the smallest (least number of carbon atoms) among those $C_{12}$-$C_{24}$ hydrocarbons. Relatedly, then, a $C_{n+1}$ hydrocarbon may refer to a hydrocarbon having 1 more carbon atom than the $C_n$ hydrocarbon (such that a $C_n$-$C_{12}$ mixture may comprise a Ca hydrocarbon and one or more $C_{n+1}$-$C_{12}$ hydrocarbons).

An "aromatic hydrocarbon" is a hydrocarbon containing an aromatic ring compound, and includes alkyl-substituted aromatic ring compounds. For instance, a $C_6$ aromatic hydrocarbon is an aromatic ring-containing hydrocarbon having 6 carbon atoms, such as benzene. Similarly, a $C_7$ aromatic hydrocarbon refers to a hydrocarbon compound containing an aromatic ring and having 7 carbon atoms, such as toluene. Thus, a "$C_6$-$C_{12}$ aromatic hydrocarbon," for example, is a hydrocarbon having 6-12 carbon atoms and containing an aromatic ring. Such hydrocarbons include, but are not necessarily limited to: benzene, toluene, ethylbenzene, xylene, diethylbenzene, propylbenzene, methylpropylbenzene, butylbenzene, and alkyl naphthalenes. Where an aromatic hydrocarbon is referred to as a "precursor aromatic hydrocarbon," the term "precursor" is meant only as a reference of convenience, denoting that the aromatic hydrocarbon will be subjected to one or more reactions.

A "cycloalkylaromatic compound" is a particular type of aromatic hydrocarbon comprising an aromatic ring (generally benzene) with a cycloalkyl substitution thereon. As used herein, "cycloalkyl substitution" or "cycloalkyl-substituted" refer to a compound in which one or more hydrogen atoms in the referenced hydrocarbon is replaced by a cyclic alkyl moiety, such as cyclopentyl, cyclohexyl, and the like. The cyclic alkyl moiety furthermore may itself contain one or more alkyl substitutions thereon. An "alkyl substitution" or "alkyl-substituted" hydrocarbon is one in which a hydrogen of the referenced hydrocarbon has been replaced with an alkyl moiety, such as methyl, ethyl, propyl, etc. Thus, a cycloalkylaromatic compound is an aromatic ring with one or more cyclic alkyl moieties substituted thereon, with the cyclic alkyl moieties themselves also optionally having one or more alkyl substitutions. Particular examples include cyclohexylbenzene (a $C_{12}$ alkylaromatic compound) and $C_{13}$-$C_{24}$ alkyl-substituted cyclohexylbenzenes (i.e., a cyclohexylbenzene containing a substituted alkyl moiety in place of one or more hydrogens on either the phenyl or cyclohexane moiety). Particularly contemplated $C_{13}$-$C_{24}$ alkyl-substituted cyclohexylbenzenes include (methylcyclohexyl) toluene, (dimethylcyclohexyl)xylene, and the like. Also contemplated are $C_{16}$-$C_{24}$ cycloalkylaromatic compounds comprising a naphthyl and/or decalin moiety, such as cyclohexylnapthalene (a $C_{16}$ substituted cycloalkylaromatic compound comprising a naphthyl moiety), and/or naphthyldecalin (a $C_{20}$ cycloalkylaromatic compound including both a naphthyl and decalin moiety). Either or both rings of such fused-ring structures may further contain an alkyl substitution. Further, unless otherwise noted, reference to an alkyl-substituted compound such as an alkyl-substituted aromatic hydrocarbon (e.g., xylene) includes any and all regioisomers of the referenced compound (e.g., p-xylene, m-xylene, and o-xylene).

A "dicycloalkylaromatic compound" is a particular subset of cycloalkylaromatic compound in which two hydrogens of the aromatic ring are substituted with cyclic alkyl moieties. Particular examples include dicyclohexylbenzene and alkyl-substituted dicyclohexylbenzenes (e.g., $C_{19}$ to $C_{36}$ alkyl-substituted dicyclohexylbenzenes, comprising one or more alkyl groups substituted onto any of the cyclohexyl rings and/or the aromatic ring).

As used herein, "biphenyl compounds" refer to biphenyl and/or substituted biphenyls. Thus, a $C_{12}$-$C_{24}$ biphenyl compound is a biphenyl or substituted biphenyl compound having 12-24 carbon atoms. Particularly contemplated are alkyl-substituted biphenyls, examples of which include biphenyl, dimethylbiphenyl, diethylbiphenyl, tetramethylbiphenyl, tetraethylbiphenyl, and so forth. Further, as with the cycloalkylaromatic compounds discussed above, also contemplated within this definition are biphenyl compounds in which either or both phenyl ring is substituted with a fused phenyl ring, such as in the case of a binaphthyl or alkyl-substituted binaphthyl compound.

Similarly, a "terphenyl compound" refers to terphenyl and/or substituted terphenyls, with $C_{19}$ to $C_{36}$ alkyl-substituted terphenyls being particularly contemplated.

Likewise, a "diphenyl oxide compound" refers to a diphenyl oxide and/or substituted diphenyl oxide, such as an alkyl-substituted diphenyl oxide (containing one or more alkyl substitutions on either or both phenyl rings of the diphenyl oxide).

First Aromatic Composition and Uses Thereof

The first aromatic compositions according to various embodiments herein comprises one or more of the following: (i) one or more cycloalkylaromatic compounds; (ii) one or more dicycloalkylaromatic compounds; (iii) one or more biphenyl compounds; (iv) one or more terphenyl compounds; and (v) one or more diphenyl oxide compounds.

Preferably, the first aromatic composition includes compounds formed via hydroalkylation and/or transalkylation (described in greater detail below) of one or more precursor aromatic hydrocarbons. A precursor aromatic hydrocarbon could be any aromatic compound, such as benzene, toluene, xylene, trimethylbenzene, ethylbenzene, diethylbenzene, cumene, tert-butyl benzene, and the like. In some embodiments, the precursor aromatic hydrocarbons are each independently selected from the group consisting of benzene and $C_7$ to $C_{12}$ alkylbenzenes. Precursor aromatic hydrocarbons of particular interest in the present disclosure include benzene, toluene, and xylene due to their prevalence as feedstocks for various useful processes.

As detailed below, the hydroalkylation processes to which single-ring $C_n$ precursor aromatic hydrocarbons (e.g., benzenes and alkyl-substituted benzenes) are provided tend to yield product streams comprising $C_{2n}$ cycloalkylaromatic compounds and $C_{3n}$ dicycloalkylaromatic compounds, generally with the same alkyl substitution (or lack thereof) on each of the two (or three) rings of such compounds. Other cycloalkylaromatic isomers are formed as byproducts (e.g., methylcyclopentyl benzene). Transalkylation may also be used to form product streams comprising $C_{2n}$ cycloalkylaromatic compounds and $C_{3n}$ dicycloalkylaromatic compounds, but such product streams may also comprise cycloalkylaromatic and/or dicycloalkylaromatic compounds with alkyl substitutions on only one of the 2 rings (or only 2 of the 3 rings), as detailed below.

Accordingly, the first aromatic composition of some embodiments includes one or more $C_{12-24}$ cycloalkylaromatic compounds. In particular embodiments, each cycloalkylaromatic compound is independently selected from the group consisting of cyclohexylbenzene, methylcyclopentylbenzene, and $C_{13}$ to $C_{24}$ alkyl-substituted cyclohexylbenzenes. In some preferred embodiments, the cycloalkylaromatic compounds are each selected from cyclohexylbenzene, (methylcyclohexyl)toluene, (dimethylcyclohexyl)xylene, and methylcyclopentylbenzene. In certain embodiments, the cycloalkylaromatic compound comprises either cyclohexylbenzene or (methylcyclohexyl)toluene. In other embodiments, the cycloalkylaromatic compound also or instead comprises methylcyclopentylbenzene.

Likewise, the first aromatic composition may further (or may instead) comprise one or more $C_{18-36}$ dicycloalkylaromatic compounds. In particular embodiments, each dicycloalkylaromatic compound is independently selected from the group consisting of dicyclohexylbenzene and $C_{19}$ to $C_{36}$ alkyl-substituted dicyclohexylbenzenes. In some preferred embodiments, the cycloalkylaromatic compounds are each selected from dicyclohexylbenzene, di(methylcyclohexyl)toluene, and di(dimethylcyclohexyl)xylene.

At least a portion of the aforementioned hydroalkylation and/or transalkylation product streams may be subjected to further reaction (e.g., dehydrogenation, also described in more detail below) to yield corresponding biphenyl and terphenyl compounds. Therefore the first aromatic composition may also or instead comprise one or more biphenyl compounds and/or one or more terphenyl compounds.

The biphenyl compounds are preferably selected from biphenyl and $C_{13}$ to $C_{24}$ alkyl-substituted biphenyl compounds, particularly biphenyl, dimethyl biphenyl, and tetramethyl biphenyl. The terphenyl compounds are preferably selected from terphenyl and $C_{19}$ to $C_{36}$ terphenyl compounds, particularly m- and o-terphenyl (and/or $C_{21-24}$ methyl-substituted variants comprising one or two methyl substitutions on each aromatic ring of such terphenyls).

Finally, portions of the hydroalkylation product streams of some embodiments may also be subjected to further oxidation and cleavage (described below) to form phenol and/or alkyl-substituted phenols. These phenols may be dehydrated to yield diphenyl oxide compounds. Thus, the first aromatic composition of some embodiments comprises diphenyl oxide and/or alkyl-substituted diphenyl oxide compounds (alone or in addition to any one or more of the aforementioned components of the first aromatic composition).

In general, the first aromatic composition may be blended with other compounds to form a useful blend. Many potential blends may be formed, but two in particular are noted as preferred embodiments herein: blending with a second aromatic composition to form a blended aromatic fluid composition (which may be useful, e.g., as an aromatic solvent, such as an agricultural solvent for pesticides, herbicides, and the like); and blending components of the first aromatic composition together (with or without additional components) to form a high temperature heat transfer fluid (HTHTF).

Turning first to blended aromatic fluid compositions, according to such embodiments, the first aromatic compositions according to various embodiments may be blended into a second aromatic composition, e.g., an aromatic solvent such as A-200 or its equivalents, and/or with any one or more components of an A-200 solvent (or equivalent aromatic solvent) to form the blended aromatic fluid. Examples of such aromatic solvent components include naphthalenes, alkylnaphthalenes, and alkylbenzenes (with preferred components including alkylnaphthalenes and alkylbenzenes). Thus, methods according to some embodiments include blending a first aromatic composition (e.g., an aromatic composition according to any of the aforementioned embodiments) with a second aromatic composition. The second aromatic composition may comprise naphthalene and/or one or more alkylnaphthalenes and/or one or more alkylbenzenes. Particular examples of alkylnaphthalenes according to some embodiments include: 1-methylnaphthalene, 2-methylnaphthalene, 2-ethylnaphthalene, dimethyl naphthalenes, and trimethyl naphthalenes. Particular examples of alkylbenzenes include toluene, xylenes, trimethylbenzenes, ethylbenzenes, diethylbenzenes, and the like.

In particular embodiments, the second aromatic composition comprises 1-methylnaphthalene, 2-methylnaphthalene, 2-ethylnaphthalene, dimethyl naphthalene, and trimethyl naphthalene. The second aromatic composition of such embodiments may further comprise naphthalene, and may also or instead further comprise one or more alkylbenzenes (e.g., toluene, xylene, ethylbenzene, diethylbenzene). In certain of these embodiments, the components of the second aromatic composition are present at the following wt % s, by weight of the second aromatic composition: 1-methylnaphthalene (8-18 wt %, such as 13 wt %); 2-methylnaphthalene (21-31 wt %, such as 26 wt %); 2-ethylnaphthalene (0.1 to 5 wt %, such as 2 wt %); dimethyl naphthalene (13-23 wt %, such as 18 wt %); and trimethyl naphthalene (2-12 wt %, such as 7 wt %); and, optionally, alkylbenzenes (0-15 wt %) and/or naphthalene (0-15 wt %).

More generally, in particular embodiments, any first aromatic composition comprising compounds having boiling points between 200° C. and 300° C. (preferably between 220° C. and 290° C.) may be blended with a second aromatic composition (e.g., an aromatic solvent, or a component thereof). Therefore, some embodiments' include blending one or more hydrocarbons having boiling points between 200° C. and 300° C. (preferably between 220° C. and 290° C.) with one or more compounds of a second aromatic composition according to the above-described embodiments of second aromatic compositions.

In some embodiments, particularly preferred first aromatic compositions for blending with a second aromatic composition include cycloalkylaromatic compounds (e.g., cyclohexylbenzenes and/or (methylcyclohexyl)toluene) and dicycloalkylaromatic compounds (e.g., di-cyclohexylbenzene and/or di(methylcyclohexyl)toluene). Such first aromatic compositions may further include one or more biphenyl or terphenyl compounds.

Turning now to HTHTF blends, methods of some embodiments include utilizing a first aromatic composition in HTHTF applications, such as by blending the components of the first aromatic composition together (with or without additional components), with optional purification of the first aromatic composition prior to blending, and/or purification of the resulting blend. Purifying may include removal of any one or more undesired impurities resulting from the process of obtaining the first aromatic composition, e.g. by distillation (such as fractional distillation). Preferably, purification removes compounds other than biphenyl compounds, terphenyl compounds, and diphenyl oxide compounds; although in some embodiments, purification also does not remove cycloalkylaromatic and dicycloalkylaromatic compounds. Conveniently, purification may include any separation process useful for isolating the just-noted compounds (e.g., distillation, such as fractional distillation; adsorption; absorption; membrane separations; flowing through molecular sieves; and the like). For example, purification may remove non-aromatic components such as paraffins, olefins, or cycloparaffins, or small levels of heavy components with four or more rings (e.g., cyclic hydrocarbons having four or more rings), which may have higher tendency for thermal degradation.

In yet other embodiments, a first aromatic composition may be provided directly as a HTHTF without any further steps (blending or purification, or the like).

Particularly useful first aromatic compositions for HTHTF applications comprise one or more of the following: biphenyl compounds, terphenyl compounds, and diphenyl oxide compounds. In some embodiments, the HTHTF formed by such first aromatic compositions comprises at least 90 wt %, preferably at least 95 wt %, more preferably at least 99 wt % of biphenyl and terphenyl compounds, combined. In yet other embodiments, such HTHTF may comprise at least 90, 95, or 99 wt % of biphenyl, terphenyl, and diphenyl oxide compounds, combined. In yet other embodiments, however, a first aromatic composition for HTHTF applications may further include one or more cycloalkylaromatic compounds and/or one or more dicycloalkylaromatic compounds (such that the combined weight of cycloalkylaromatic, dicycloalkylaromatic, biphenyl, terphenyl, and diphenyl oxide compounds is at least 90, 95, or 99 wt %). In each of the aforementioned cases, the wt % s are based on the total weight of the HTHTF. Processes employing some purification of the first aromatic composition to form the HTHTF are particularly useful in obtaining HTHTFs according to the just-noted embodiments.

Preferred first aromatic compositions for HTHTF applications comprise m-terphenyls and o-terphenyls, as these compounds have melting points at standard pressure of 84-88° C. and 56-59° C., respectively. These melting points are similar to biphenyl (currently used extensively in HTHTF applications), therefore indicating similar cold flow characteristics; however, m-terphenyl and o-terphenyl have significantly higher boiling points than biphenyl (379° C. and 337° C., respectively, as compared to 255° C. for biphenyl at standard pressure), indicating a greater range of stability. In general, for HTHTF applications, low melting point and high boiling point are desired (e.g., a greater range between melting point and boiling point is preferred). Thus, in preferred embodiments, where terphenyl compounds are present in the HTHTF, preferably at least 90 wt % (more preferably at least 95 wt %, such as at least 99 wt %) of the terphenyl compounds are present as either the m- or the o-isomers. Again, processes employing some purification of the first aromatic composition are particularly useful in obtaining this desired amount of terphenyl isomers.

As noted, the components of the first aromatic composition may be blended together to form the high temperature heat transfer fluid, or blended with one or more additional heat transfer fluid components (with or without purification of the first aromatic composition or of the blended composition and heat transfer fluid). The one or more additional heat transfer fluid components are preferably selected from the group consisting of biphenyl compounds, diphenylethers, terphenyl compounds, and any combination thereof. In a preferred embodiment, the one or more additional heat transfer fluid components include biphenyl.

Whether blended together, blended with one or more additional heat transfer fluid components, or provided directly as a HTHTF, first aromatic compositions provided herein may afford distinct advantages when utilized in HTHTF applications. In addition to being advantageously sourced from one of the processes described below, they may offer a broader operating window for HTHTF applications (e.g., the lower vapor pressures of such components of first aromatic compositions may extend the operating window for HTHTFs to even higher temperatures than conventional HTHTFs, such as in excess of 400° C., 500° C., 600° C., or even 700° C.). Further, some first aromatic compositions may minimize undesirable odors commonly associated with current HTHTFs. Also or instead, first aromatic compositions according to some embodiments may advantageously avoid benzene as a major decomposition product. HTHTHFs employing such first aromatic compositions may also exhibit enhanced heat transfer characteristics and/or anti-corrosion properties as compared to conventional HTHTFs. Formulations may also include anti-oxidants or other minor additives that are known in the art for improving HTHTF performance and stability.

Obtaining the First Aromatic Composition

The first aromatic compositions described herein are preferably obtained through a process comprising hydroalkylation and/or transalkylation of one or more precursor aromatic hydrocarbons.

Hydroalkylation is a two-stage catalytic reaction in which an aromatic compound is partially hydrogenated to produce a cyclic olefin intermediate, which then reacts, in situ, with the aromatic compound to produce a cycloalkylaromatic product. Particularly useful examples according to embodiments of the present invention include the hydroalkylation of benzene to cyclohexylbenzene (and various byproducts including dicyclohexylbenzene, methylcyclopentylbenzene, and cyclohexane), and the hydroalkylation of toluene to (methylcyclohexyl)toluene (and byproducts such as di(m-ethylcyclohexyl)toluene).

In general, then, hydroalkylation according to various embodiments includes contacting a precursor aromatic hydrocarbon (e.g., benzene or an alkylbenzene) with hydrogen in the presence of a hydroalkylation catalyst so as to form a hydroalkylation product effluent comprising a cycloalkylaromatic compound. As shown in overall Reaction-1 below, the precursor aromatic hydrocarbon will undergo the aforementioned two-stage reaction such that the resulting cycloalkylaromatic compound will contain substitutions on each of its two rings (one aromatic, one cycloalkyl) corresponding to any substitutions present on the precursor aromatic hydrocarbon:

(Reaction-1).

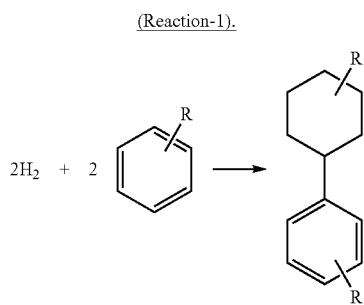

R as illustrated in Reaction-1 may be H or an alkyl group. Preferably, it is H or a $C_1$ to $C_6$ alkyl group, in particular H, methyl, or ethyl. Where R of Reaction-1 is H, the illustrated hydroalkylation reaction corresponds to the hydroalkylation of benzene to cyclohexylbenzene. Where R of Reaction-1 is methyl, the illustrated hydroalkylation reaction corresponds to the hydroalkylation of toluene to (methylcyclohexyl) toluene, and so on for any other substitution. Of course, poly-substituted benzenes are also contemplated as precursor aromatic hydrocarbons, in which case each ring of the resulting cycloalkylaromatic compound will have the same two (or three, four, or five) substitutions thereon (e.g., as in the case of hydroalkylation of xylene to (dimethylcyclohexyl)xylene). The substitutions are not necessarily always in the same locations on each ring relative to the point of bonding between the rings, and therefore many different positional isomers of the cycloalkylaromatic compound may be produced.

The hydroalkylation product effluent may further comprise a dicycloalkylaromatic compound, which may be generated when some portion of the cycloalkylaromatic compound further reacts with a cyclic olefin intermediate of the hydroalkylation reaction, thereby forming the dicycloalkylaromatic compound, as illustrated in Reaction-2 below:

(Reaction-2).

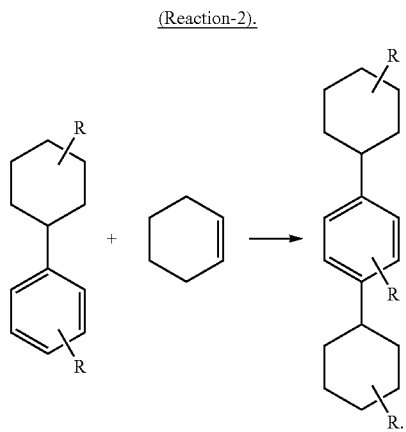

R may be any moiety as illustrated above with respect to Reaction-1, with preference once again being given for R=H or a $C_6$ to $C_{12}$ alkyl group (particularly H, methyl, or ethyl). As with the cycloalkylaromatic compound, the same substitution (or lack thereof) will appear at some position on each ring of the dicycloalkylaromatic compound. The hydroalkylation product effluent may comprise other byproducts such as cyclohexane or alkyl-substituted cyclohexane (representing complete hydrogenation of the aromatic ring of the precursor aromatic hydrocarbon), and isomerization products of the principal cycloalkylaromatic compound, such as other cycloalkylaromatic compounds (e.g., methylcyclopentylbenzene, produced during hydroalkylation of benzene to cyclohexylbenzene). Aromatic byproducts such as the methylcyclopentylbenzene may be particularly useful in first aromatic compositions of various embodiments of the present invention.

In general, then, it can be seen that hydroalkylation of a $C_n$ benzene or alkylbenzene produces a $C_{2n}$ cycloalkylaromatic compound, and/or $C_{3n}$ dicycloalkylaromatic compounds. In particular embodiments, the precursor aromatic hydrocarbon preferably comprises benzene and/or $C_7$ to $C_{12}$ alkylbenzenes, such that the cycloalkylaromatic compounds comprise cyclohexylbenzene and/or $C_{14}$ to $C_{24}$ alkyl-substituted cyclohexylbenzenes, and further such that the dicycloalkylaromatic compounds comprise dicyclohexylbenzene and/or $C_{21}$ to $C_{36}$ alkyl-substituted dicyclohexylbenzenes.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. The molar ratio of hydrogen to aromatic feed is typically from about 0.15:1 to about 15:1.

The catalyst employed in the hydroalkylation reaction is a bifunctional catalyst comprising a hydrogenation component (e.g., a hydrogenation metal selected from group 10 of the Periodic Table of the Elements, with palladium being particularly advantageous) and a solid acid alkylation component, typically a molecular sieve. The catalyst may also include a binder such as clay, silica and/or metal oxides. In general, suitable hydroalkylation catalysts include those described in Paragraphs [0025]-[0029] of WIPO Publication No. 2014/159104 (published 2 Oct. 2014, with International Filing Date of 7 Mar. 2014), which is incorporated by reference herein.

A particularly preferred hydroalkylation catalyst, as noted therein, comprises a molecular sieve of the MCM-22 family. Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697) and mixtures thereof.

For more details of hydroalkylation of benzene according to some embodiments, see U.S. Pat. Nos. 6,730,625 and 7,579,511; and WIPO Publication Nos. WO2009/131769, and WO2009/128984. For more details of hydroalkylation of alkylbenzenes such as toluene and/or xylene according to some embodiments, see U.S. Patent Publication No. 2014/0275609.

Transalkylation may similarly be used to obtain cycloalkylaromatic compounds and/or dicycloalkylaromatic compounds from an aromatic precursor hydrocarbon; however, unlike with the hydroalkylation reactions just described, transalkylation reactions may produce cycloalkylaromatic and dicycloalkylaromatic compounds having asymmetrical substitutions (and/or lack thereof) on each ring. As shown in Reaction-3 below, such transalkylation reactions include contacting a precursor cycloalkylaromatic compound in addition to the precursor aromatic hydrocarbon. In simplified form, the transalkylation reaction according to such embodiments essentially involves the targeted replacement of (a) the aromatic moiety of the precursor cycloalkylaromatic compound with (b) the precursor aromatic hydrocarbon. In this way, one can obtain a cycloalkylaromatic compound having one or more alkyl substitutions specifically located on the aromatic ring of the compound.

(Reaction-3).

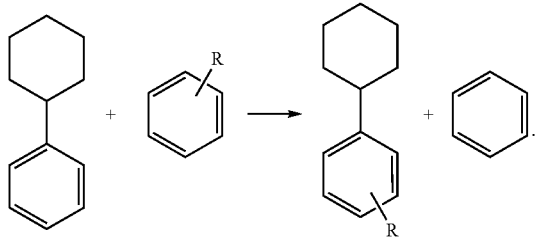

R may be any moiety as illustrated above with respect to Reaction-1 and Reaction-2, with preference once again being given for R=H or a $C_6$ to $C_{12}$ alkyl group, in particular H, methyl, or ethyl. Further, as with Reaction-1 and Reaction-2, 1, 2, 3, 4, or 5 R groups (each being the same or different from any other R-group) may be present on the precursor aromatic hydrocarbon, and therefore on the aromatic ring of the cycloalkylaromatic product. Furthermore, as with the hydroalkylation reactions described above, additional alkylation of the cycloalkylaromatic product with the precursor aromatic hydrocarbon may lead to a dicycloalkylaromatic compound having the same substitution(s) (if any) on the central aromatic ring moiety and on one of the appurtenant cyclohexyl ring moieties, per the illustration of Reaction-4:

(Reaction-4).

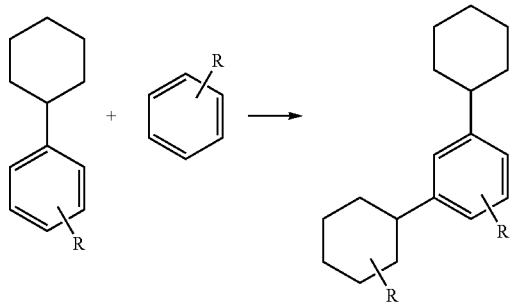

Where mixtures of different precursor aromatic hydrocarbons are used as feed, different aromatic groups may be substituted in place of the aromatic moiety of a cycloalkylaromatic precursor compound, and/or different aromatic groups may react with a cycloalkylaromatic compound to form a dicycloalkylaromatic compound having different substitutions on each of the three ring moieties. As such, it can be seen that the transalkylation reaction of various embodiments can convert a $C_n$ precuror aromatic hydrocarbon (e.g., benzene or alkylbenzene) into a $C_{n+6}$ cycloalkylaromatic compound, and/or into a $C_{2n+6}$ dicycloalkylaromatic compound. In particular embodiments, the precursor aromatic hydrocarbon preferably comprises benzene and/or $C_7$ to $C_{12}$ alkylbenzenes, such that the cycloalkylaromatic compounds comprise cyclohexylbenzene and/or $C_{13}$ to $C_{24}$ alkyl-substituted cyclohexylbenzenes, and further such that the dicycloalkylaromatic compounds comprise dicyclohexylbenzene and/or $C_{19}$ to $C_{36}$ alkyl-substituted dicyclohexylbenzenes.

The transalkylation reaction can be conducted over a wide range of conditions but in most embodiments is effected at a temperature from about 75° C. to about 250° C., such as from about 100° C. to about 200° C., for example about 125° C. to about 160° C.; and a pressure from about 100 to about 3550 kPa-absolute, such as from about 1000 to about 1500 kPa-absolute.

The transalkylation catalyst may be a solid acid catalyst, such as a molecular sieve and in particular a molecular sieve having a large pore molecular sieve having a Constraint Index (as defined in U.S. Pat. No. 4,016,218) less than 2. Suitable large pore molecular sieves include zeolite beta, zeolite Y, Ultrastable Y (USY), Dealuminated Y (Deal Y), mordenite, ZSM-3, ZSM-4, ZSM-18, ZSM-20, and mixtures thereof, with zeolite beta and zeolite Y being preferred in some embodiments. Other suitable molecular sieves include molecular sieves of the MCM-22 family. In general, a transalkylation catalyst may include any solid acid alkylation component in accordance with the bifunctional hydroalkylation catalyst described above.

Whether hydroalkylation or transalkylation (or a combination thereof) is employed, preferably each of the hydroalkylation reaction effluent and the transalkylation reaction effluent comprise one or more cycloalkylaromatic compounds and one or more dicycloalkylaromatic compounds. Therefore, methods according to some embodiments include obtaining at least a portion of the first aromatic compositions of such embodiments from at least a portion of the hydroalkylation reaction effluent and/or the transalkylation reaction effluent.

However, further processes may be carried out on a further portion of (or on all of) the hydroalkylation reaction effluent and/or transalkylation reaction effluent. In particular, methods according to some embodiments include dehydrogenating at least a portion of the hydroalkylation reaction effluent and/or transalkylation reaction effluent to obtain one or more biphenyl compounds and/or triphenyl compounds. For an example of dehydrogenation of cycloalkylaromatic compounds to corresponding biphenyl compounds, see U.S. Patent Publication No. 2014/0275609.

The dehydrogenation is conveniently conducted at a temperature from about 200° C. to about 600° C. and a pressure from about 100 kPa to about 3550 kPa (atmospheric to about 500 psig) in the presence of a dehydrogenation catalyst. A suitable dehydrogenation catalyst comprises one or more elements or compounds thereof selected from group 10 of the Periodic Table of the Elements, for example Pt, on a support, such as silica, alumina, or carbon. In one embodiment, the group 10 element is present in amounts from about 0.1 to about 5 wt % of the catalyst. Suitable dehydrogenation catalysts of some embodiments may further include tin (e.g., in amounts from about 0.01 to about 2 wt % of the catalyst, if present).

It can readily be seen that dehydrogenation of a cycloalkylaromatic compound will lead to the corresponding biphenyl compound, where the cycloalkyl ring of the cycloalkylaromatic compound is dehydrogenated to an aromatic ring. Advantageously, the alkyl substitutions (if any) on the cycloalkylaromatic compound will predominantly carry through and be present on the biphenyl product of the dehydrogenation. Similarly, dicycloalkylaromatic compounds will dehydrogenate to the corresponding terphenyl compounds.

Thus, where hydroalkylation and/or transalkylation effluents comprise (i) cycloalkylaromatic compounds selected from the group consisting of cyclohexylbenzene and $C_{13}$ to $C_{24}$ alkyl-substituted cyclohexylbenzenes; and/or (ii) dicycloalkylaromatic compounds selected from the group consisting of dicyclohexylbenzene and $C_{19}$ to $C_{36}$ alkyl-substituted dicyclohexylbenzenes, the dehydrogenation of such effluents will yield a dehydrogenation effluent comprising (iii) $C_{13}$ to $C_{24}$ biphenyl compounds corresponding to the cycloalkylaromatic compounds, and/or (iv) $C_{19}$ to $C_{36}$ terphenyl compounds corresponding to the dicycloalkylaromatic compounds.

The first aromatic compositions of some embodiments are therefore obtained by hydroalkylating and/or transalkylating precursor aromatic hydrocarbons to form a hydroalkylation reaction effluent (and/or transalkylation reaction effluent) as described above, and further by dehydrogenating at least a portion of the hydroalkylation reaction effluent and/or transalkylation reaction effluent to form a dehydrogenation reaction effluent. At least a portion of the dehydrogenation reaction effluent is obtained as the first aromatic composition. The dehydrogenation reaction effluent may optionally be subjected to one or more separations processes to remove compounds other than the biphenyl and/or terphenyl compounds, and/or it may be blended with a portion of the hydroalkylation and/or transalkylation reaction effluent (not provided to the dehydrogenation reaction) to form a first aromatic composition comprising cyclo alkyl aromatic compounds and/or dicycloalkyaromatic compounds in addition to the biphenyl and/or terphenyl compounds. Alternatively, the dehydrogenation effluent may be provided as the first aromatic composition without further blending or other processing such as separations.

Alternatively or in addition, at least a portion of the hydroalkylation or transalkylation reaction effluent of some embodiments (other than any portion(s) withdrawn to form first aromatic compositions, and/or any portion(s) subjected to dehydrogenation) may be subjected to oxidation and cleavage to form a cleavage reaction mixture comprising phenol or alkyl-substituted phenol. Such processes are consistent with processes for the co-production of phenol and cyclohexanone via hydroalkylation of benzene to cyclohexylbenzene, as described in, e.g., U.S. Pat. Nos. 6,730,625 and 7,579,511, WIPO Publication Nos. WO2009/131769, WO2009/128984, and WO 2014/189623, each of which is hereby incorporated herein by reference.

For instance, as described in Paragraphs [0052]-[0058] of WO 2014/189623 (incorporated herein by reference), cyclohexylbenzene may be oxidized with an oxygen-containing gas in the presence of an oxidation catalyst (e.g., a cyclic imide such as N-hydroxyphthalimide or NHPI), forming an oxidation reaction effluent comprising cyclohexylbenzene-hydroperoxide. Other alkyl-substituted cyclohexylbenzenes may likewise be oxidized to form corresponding alkyl-substituted cyclohexylbenzene-hydroperoxides.

At least a portion of the oxidation reaction effluent is subjected to a cleavage reaction, e.g., by contact with an acid catalyst (solid acid or liquid acid, such as sulfuric acid). Where cyclohexylbenzene-hydroperoxide is present in the oxidation reaction effluent (e.g., from oxidation of cyclohexylbenzene), the cleavage reaction product will comprise cyclohexanone and phenol. See Paragraphs [0061]-[0082] of WO 2014/189623, incorporated herein by reference; and Paragraphs [0056]-[0067] of WO 2014/209557, also incorporated herein by reference. Correspondingly, where alkyl-substituted cyclohexylbenzene hydroperoxides are present in the oxidation reaction effluent, the cleavage reaction will yield alkyl-substituted phenols and alkyl-substituted cyclohexanones.

The cleavage reaction effluent optionally may be treated, e.g., to remove one or more contaminants formed during the reactions forming the cleavage reaction effluent. Detailed description of the contaminant treatment process can be found, e.g., in International Publication WO2012/036822A1, the relevant content of which is incorporated herein by reference in its entirety. The cleavage reaction effluent may also or instead be subjected to one or more separation processes to obtain phenol and/or alkyl-substituted phenol from the effluent. However, because cyclohexanone and phenol form an azeotrope, separation of the two may be difficult. Extractive distillation may be utilized, e.g., in accordance with the description of WIPO publications WO2013/165656A1 and WO2013/165659, the contents of which are incorporated herein by reference in their entirety.

Following optional treatment and/or separation, at least a portion of the cleavage reaction effluent comprising at least a portion of the phenol or alkyl-substituted phenol is further subjected to dehydration reaction to form a diphenyl oxide compound (e.g., diphenyl oxide or alkyl-substituted diphenyl oxides) from the phenol or alkyl-substituted phenol. The dehydration reaction is carried out by contacting the phenol or alkyl-substituted phenol with a dehydration catalyst, thereby forming the corresponding diphenyl oxide compound(s). Suitable dehydration catalysts include acids, such as H-forms of molecular sieves and acidic alumina.

Thus, the first aromatic compositions of some embodiments may comprise (or may further comprise) a diphenyl oxide compound formed according to such processes.

PARTICULAR PROCESS EMBODIMENTS

Particular examples of processes according to certain embodiments include the specific cases of processes involving (i) hydroalkylation of benzene to cyclohexylbenzene and (ii) hydroalkylation of toluene and/or xylene to (methylcyclohexyl)toluene and/or (dimethylcyclohexyl)xylene.

Turning first to hydroalkylation of benzene, processes according to certain exemplary embodiments include:
(i) hydroalkylating benzene to form a hydroalkylation reaction effluent comprising cyclohexylbenzene, dicyclohexylbenzene, and methylcyclopentylbenzene;
(ii) oxidizing at least a portion of the hydroalkylation reaction effluent, forming an oxidation reaction effluent comprising cyclohexylbenzene hydroperoxide;
(iii) optionally, dehydrogenating an additional portion of the hydroalkylation reaction effluent, forming a dehydrogenation reaction effluent comprising one or more of biphenyl and terphenyl (including m-terphenyl, o-terphenyl, and p-terphenyl);

(iv) cleaving at least a portion of the oxidation reaction effluent, forming a cleavage reaction product comprising cyclohexanone and phenol;

(v) optionally, dehydrating at least a portion of the cleavage reaction product, forming a dehydration reaction effluent comprising diphenyl oxide; and (vi) forming a first aromatic composition from one or more of: (a) a further portion of the hydroalkylation reaction effluent comprising cyclohexylbenzene and/or dicyclohexylbenzene; (b) a further portion of the dehydrogenation reaction effluent comprising biphenyl and/or terphenyl; and (c) a portion of the dehydration reaction effluent comprising diphenyl oxide.

Particularly preferred first aromatic compositions according to such embodiments comprise one or more of cyclohexylbenzene, methylcyclopentylbenzene, biphenyl, m-terphenyl, and o-terphenyl. In some such embodiments, the first aromatic composition comprises m-terphenyl and o-terphenyl. In yet other embodiments, the first aromatic composition comprises cyclohexylbenzene and/or methylcyclopentylbenzene.

Turning now to hydroalkylation of toluene/xylene, processes according to certain exemplary embodiments include:

(i) hydroalkylating toluene, forming a hydroalkylation reaction effluent comprising one or more of (methylcyclohexyl)toluene and di(methylcyclohexyl)toluene;

(ii) dehydrogenating at least a portion of the hydroalkylation reaction effluent so as to obtain a dehydrogenation reaction effluent comprising one or more of dimethylbiphenyl and trimethylterphenyl (including any regioisomer thereof, wherein each phenyl ring of the dimethylbiphenyl and/or trimethylterphenyl has one methyl substitution thereon); and (iii) forming a first aromatic composition from one or more of: (a) a further portion of the hydroalkylation reaction effluent comprising (methylcyclohexyl)toluene and/or di(methylcyclohexyl)toluene; (b) at least a portion of the dehydrogenation reaction effluent comprising dimethylbiphenyl and/or trimethylterphenyl.

Particularly preferred first aromatic compositions according to such embodiments comprise one or more of (methylcyclohexyl)toluene, di(methylcyclohexyl)toluene, dimethylbiphenyl, m-trimethylterphenyl, and o-trimethylterphenyl (wherein each phenyl ring of the recited biphenyl and/or terphenyl isomers contains a methyl substitution). In some such embodiments, the first aromatic composition comprises m-trimethylterphenyl and o-trimethylterphenyl. In yet other embodiments, the first aromatic composition comprises (methylcyclohexyl)toluene.

At least a portion of the first aromatic composition formed according to either of the above-described embodiments may then be blended with a second aromatic composition according to the previously-described embodiments of second aromatic compositions. Alternatively or instead, the components of at least a portion of the first aromatic composition are blended together (and, optionally, purified) to form a high temperature heat transfer fluid. Optionally, the components of the first aromatic composition are further blended with one or more additional heat transfer fluid components, as previously described.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. All documents described herein are incorporated by reference herein, including any priority documents and/or testing procedures to the extent they are not inconsistent with this text. Likewise, the term "comprising" is considered synonymous with the term "including." Whenever a composition, an element or a group of elements is preceded with the transitional phrase "comprising," it is understood that—unless the context plainly dictates otherwise—we also contemplate the same composition or group of elements with transitional phrases "consisting essentially of," "consisting of," "selected from the group of consisting of," or "is" preceding the recitation of the composition, element, or elements and vice versa.

We claim:

1. A process comprising:
    (a) obtaining a first aromatic composition from one or more precursor aromatic hydrocarbons, wherein the first aromatic composition comprises one or more of:
        (i) one or more cycloalkylaromatic compounds; (ii) one or more dicycloalkylaromatic compounds; (iii) one or more biphenyl compounds; and (iv) one or more terphenyl compounds; and
    (b) blending the first aromatic composition with a second aromatic composition comprising 8-18 wt % 1-methylnaphthalene, 21-31 wt % 2-methylnaphthalene, 0.1 to 5 wt % 2-ethylnaphthalene, 13-23 wt % dimethyl naphthalene, 2-12 wt % trimethylnaphthalene, 0-15 wt % alkylbenzenes, and 0-15 wt % naphthalene, thereby forming a blended aromatic fluid composition;
    wherein obtaining the first aromatic composition comprises one of:
        (a-1) contacting a hydroalkylation feed comprising the one or more aromatic hydrocarbons with hydrogen in the presence of a MCM-22 hydroalkylation catalyst so as to produce a hydroalkylation reaction effluent comprising (i) the one or more cycloalkylaromatic compounds and (ii) the one or more dicycloalkylaromatic compounds; and
        (a-2) contacting a transalkylation feed comprising the one or more aromatic hydrocarbons with a precursor cycloalkylaromatic compound in the presence of a transalkylation catalyst comprising zeolite beta, zeolite Y, Ultrastable Y (USY), Dealuminated Y (Deal Y), mordenite, ZSM-3, ZSM-4, ZSM-18, ZSM-20, or mixtures thereof, so as to produce a transalkylation reaction effluent comprising the one or more cycloalkylaromatic compounds and the one or more dicycloalkylaromatic compounds.

2. The process of claim 1, wherein the first aromatic composition comprises the one or more biphenyl compounds and/or the one or more terphenyl compounds, and further wherein obtaining the first aromatic composition further comprises dehydrogenating at least a portion of the hydroalkylation reaction effluent or the transalkylation reaction effluent, thereby obtaining the one or more biphenyl compounds and/or the one or more terphenyl compounds.

3. The process of claim 1, wherein the first aromatic composition comprises the one or more cycloalkylaromatic compounds and/or the one or more dicycloalkylaromatic compounds.

4. The process of claim 1, wherein the first aromatic composition comprises each of the one or more cycloalkylaromatic compounds; the one or more dicycloalkylaromatic compounds; the one or more biphenyl compounds; and the one or more terphenyl compounds; and further wherein obtaining the first aromatic composition further comprises dehydrogenating a portion of the hydroalkylation reaction effluent or the transalkylation reaction effluent.

5. The process of claim 1, wherein: (i) the precursor aromatic hydrocarbons are each independently selected from the group consisting of benzene and $C_7$ to $C_{12}$ alkylbenzenes; (ii) the cycloalkylaromatic compounds are each independently selected from the group consisting of cyclohexylbenzene, methylcyclopentylbenzene, and $C_{13}$ to $C_{24}$ alkyl-substituted cyclohexylbenzenes; (iii) the dicycloalkylaromatic compounds are each selected from dicyclohexylbenzene and $C_{19}$ to $C_{36}$ alkyl-substituted dicyclohexylbenzenes; (iv) the biphenyl compounds are each independently selected from biphenyl and $C_{13}$ to $C_{24}$ alkyl-substituted biphenyl; and (v) the terphenyl compounds are each independently selected from terphenyl and $C_{19}$ to $C_{36}$ alkyl-substituted terphenyls.

6. The process of claim 1, wherein: (i) the precursor aromatic hydrocarbons comprise one or more of benzene, toluene, and xylene; (ii) the cycloalkylaromatic compounds comprise one or more of cyclohexylbenzene, methylcyclopentylbenzene, (methylcyclohexyl)toluene, and (dimethylcyclohexyl)-xylene; (iii) the dicycloalkylaromatic compounds comprise one or more of dicyclohexylbenzene, di(methylcyclohexyl)toluene, and di(dimethylcyclohexyl)-xylene; (iv) the biphenyl compounds comprise one or more of biphenyl, dimethylbiphenyl, and tetramethylbiphenyl; and (v) the terphenyl compounds comprise one or more of terphenyl, trimethylterphenyl, and hexamethylterphenyl;

wherein each of the aforementioned phenyl compounds comprises at most one methyl substitution per phenyl ring.

7. The process of claim 1, wherein: (i) the precursor aromatic hydrocarbons comprise benzene, (ii) the cycloalkylaromatic compounds comprise cyclohexylbenzene and methylcyclopentylbenzene, (iii) the dicycloalkylaromatic compounds comprise dicyclohexylbenzene, (iv) the biphenyl compounds comprise biphenyl, and (v) the terphenyl compounds comprise m-terphenyl and o-terphenyl.

8. The process of claim 1, wherein the first aromatic composition comprises methylcyclopentylbenzene.

9. The process of claim 1, wherein: (i) the precursor aromatic hydrocarbons comprise toluene, (ii) the cycloalkylaromatic compounds comprise (methylcyclohexyl)toluene, (iii) the dicycloalkylaromatic compounds comprise di(methylcyclohexyl)toluene, (iv) the biphenyl compounds comprise dimethylbiphenyl, and (v) the terphenyl compounds comprise trimethylterphenyl.

10. The process of claim 1, wherein the first aromatic composition comprises one or more of dimethylbiphenyl, m-terphenyl, o-terphenyl, m-trimethylterphenyl, and o-trimethylterphenyl.

11. A process comprising:
a) hydroalkylating benzene by contacting a feed comprising the one or more aromatic hydrocarbons with hydrogen in the presence of a MCM-22 hydroalkylation catalyst to form a hydroalkylation reaction effluent comprising cyclohexylbenzene, dicyclohexylbenzene, and methylcyclopentylbenzene;
b) oxidizing at least a portion of the hydroalkylation reaction effluent, forming an oxidation reaction effluent comprising cyclohexylbenzene hydroperoxide;
c) optionally, dehydrogenating an additional portion of the hydroalkylation reaction effluent, forming a dehydrogenation reaction effluent comprising one or more of biphenyl and terphenyl (including m-terphenyl, o-terphenyl, and p-terphenyl);
d) cleaving at least a portion of the oxidation reaction effluent, forming a cleavage reaction product comprising cyclohexanone and phenol;
e) optionally, dehydrating at least a portion of the cleavage reaction product, forming a dehydration reaction effluent comprising diphenyl oxide;
f) forming a first aromatic composition from one or more of: (i) a further portion of the hydroalkylation reaction effluent comprising one or more of cyclohexylbenzene, dicyclohexylbenzene, and methylcyclopentylbenzene; (ii) a further portion of the dehydrogenation reaction effluent comprising biphenyl and/or terphenyl; and (iii) a portion of the dehydration reaction effluent comprising diphenyl oxide; and
g) blending the first aromatic composition with a second aromatic composition comprising 8-18 wt % 1-methylnaphthalene, 21-31 wt % 2-methylnaphthalene, 0.1 to 5 wt % 2-ethylnaphthalene, 13-23 wt % dimethyl naphthalene, 2-12 wt % trimethylnaphthalene, 0-15 wt % alkylbenzenes, and 0-15 wt % naphthalene.

12. The process of claim 11, wherein the first aromatic composition is formed from the further portion of the hydroalkylation reaction effluent, and further wherein the further portion of the hydroalkylation reaction effluent comprises methylcyclopentylbenzene, such that the first aromatic composition comprises methylcyclopentylbenzene.

13. The process of claim 12, wherein the further portion of the hydroalkylation reaction effluent further comprises cyclohexylbenzene, such that the first aromatic composition further comprises cyclohexylbenzene.

* * * * *